(12) United States Patent
Levin et al.

(10) Patent No.: US 6,451,605 B1
(45) Date of Patent: Sep. 17, 2002

(54) PHARMACEUTICAL OR VETERINARY COMPOSITION

(75) Inventors: Orna Levin, Kfar Netter; David Marcos, Kibbutz Mabarot, both of (IL)

(73) Assignee: Ornaquin Ltd., Tel Aviv (IL)

( * ) Notice: Subject to any disclaimer, the term of this patent is extended or adjusted under 35 U.S.C. 154(b) by 780 days.

(21) Appl. No.: 08/625,495

(22) Filed: Mar. 29, 1996

(51) Int. Cl.$^7$ ................................................ A61K 35/78

(52) U.S. Cl. ........................ 435/725; 435/743; 435/745; 435/746

(58) Field of Search .................. 424/195.1, DIG. 10, 424/725, 743, 745, 746; 514/558, 724, 886, 887

(56) References Cited

U.S. PATENT DOCUMENTS

| | | | | |
|---|---|---|---|---|
| 4,235,889 A | * | 11/1980 | Evers | 424/195.1 |
| 4,933,371 A | * | 6/1990 | Hink et al. | 514/739 |
| 5,455,055 A | * | 10/1995 | Soltz | 426/115 |
| 5,456,745 A | * | 10/1995 | Roreger et al. | 106/128 |

FOREIGN PATENT DOCUMENTS

| | | | |
|---|---|---|---|
| GB | 1574609 | * | 9/1980 |
| GB | 2228411 | * | 8/1990 |

* cited by examiner

*Primary Examiner*—Iren Marx
(74) *Attorney, Agent, or Firm*—Mark M. Friedman

(57) ABSTRACT

A pharmaceutical or veterinary composition which includes one or more volatile oil, one or more alcohol and one or more fixed oil and/or one or more emollient ester of fatty acid derived from vegetable oils.

10 Claims, No Drawings

PHARMACEUTICAL OR VETERINARY COMPOSITION

FIELD AND BACKGROUND OF THE INVENTION

The present invention relates to a pharmaceutical or veterinary composition.

Volatile oils have for centuries been used in various ways to treat medical problems. Their use is found in folk medicine, natural therapy, aromatherapy and even in traditional (Western) medicine.

Volatile oils in connection with the present invention are those essential oils embraced by the definition in Hackh's Chemical Dictionary, 4th Edition, page 248.

A number of volatile oils found in plants are known to repel or kill insects. The volatile oils mights be part of the mechanisms which plants use to protect themselves from attack by insects and animals.

This property to kill or repel insects has also been used in medicine. For example, the use of volatile oils in the treatment of parasitic infestations is described in "The Manual of Natural Therapy" by M. Olshevsky, B. Noy and M. Zwang (Published by Facts of Life, New York, 1989). For scabies, the following treatment is suggested (pp 183, 185): "Use the essence of geranium 5% in olive oil base and massage the affected part of the skin once per day until condition improves." For lice, the following is suggested (p. 185): "Rub the whole body with the following combination in olive oil base: crushed garlic 10%, lavender essence 3%, thyme 2%, rosemary 4%. Do this treatment once per day until condition improves." Another treatment for lice suggests (p.186) using Aniseed oil or a 1:1 mixture of Sassafras oil and quassis oil.

Lice belong to the group of external parasites living on warm-blooded animals. In humans, lice are responsible for pediculosis, a parasitic infestation of the skin of the scalp, trunk or pubic areas. There are three different varieties: (1) Pediculosis pubis caused by Phthirus pubis; (2) Pediculosis corporis, caused by Pediculus humanus humanus; (3) Pediculosis capitis, caused by Pediculus humanis capitis.

In animals lice mainly affect birds.

Scabies is a common dermatitis caused by infestation with the mite Sarcoptes scabisi. It affects humans and is also found in various forms in animals such as dogs, cattle, sheep, camels and birds.

Both scabies and pediculosis are conditions which affect millions of humans world-wide. A variety of products and treatments have been tried over the years to treat scabies or lice infestations but none has succeeded in eradicating these two conditions. Epidemics of scabies and of pediculosis appear to be cyclical in nature.

The volatile oils are rather expensive. Moreover, the traditional way to use pure volatile oils is usually hampered by the tendency of these oils to often cause a burning sensation and erythema when applied to the skin. Diluting the volatile oils in a fixed oil such as olive oil may reduce these side-effects but also reduces their potency. Treatment is less effective and often requires repeated applications. (Fixed oils in connection with the present invention are those embraced by the definition in Hackh's Dictionary (Chemical). 4th Edition, page 269).

Dissolving a volatile oil in an alcohol, e.g. ethanol, retained the anti-insect properties but also retained the undesired side-effects, e.g., the burning sensation on the skin and erythema.

SUMMARY OF THE INVENTION

The pediculicidal activity of various formations was tested in the laboratory on human body louse pediculus humanus humanus according to the following methods:

Body lice were reared in the laboratory by feeding them every second day on rabbits. Lice were placed on the shaved abdomen of a white rabbit and left until they fed to satisfy. Outside the host the lice were maintained at a temperature of 30+1 degree C and relative humidity of 70+10%.

For each test 50 lice (10 males, 10 females and 30 nymphs) were placed on a 7 cm white filter paper disc (Whatman No. 2) and exposed to 1 g of the test formulation. The lice were left in contact with the formulation for 15 minutes. Thereafter they were removed and shampooed for one minute with a regular shampoo and then washed for one minute under running tap water. After treatment the lice were transferred to a fresh filter paper disc and incubated overnight at optimum temperatures and humidities. Mortality was determined after 24 hours.

DESCRIPTION OF THE PREFERRED EMBODIMENTS

In order to examine the ovicidal activity lice were allowed to oviposit on human hair. Fifty 2–6 day old eggs were tested according to the same procedure as for lice. Mortality count was made after 10 days. The testing for lice and eggs was repeated 3 times. As a control 40% ethyl alcohol was used.

Pure Rosemary Oil and Anise Oil were tested for their efficacy in killing lice. The oils were also diluted in Olive Oil or in Ethanol (95%) and efficacy in killing lice again tested. The results are shown in Table 1.

TABLE 1

| Example Number | Percentage (v/v) Volatile Oil | | Diluent (to 100% v/v) | Percentage Lice Killed | Percentage Eggs Killed |
| --- | --- | --- | --- | --- | --- |
| 1 | Rosemary Oil | 100% | — | 100% | 28.8% |
| 2 | Anise Oil | 100% | — | 100% | 79.7% |
| 3 | Rosemary Oil | 33% | Olive Oil | 34% | — |
| 4 | Anise Oil | 33% | Olive Oil | 68% | — |
| 5 | Rosemary Oil | 33% | Ethanol (95%) | 100% | 42% |
| 6 | Anise Oil | 33% | Ethanol (95%) | 100% | 72% |
| 7 | Rosemary Oil | 33% | Olive Oil | 100% | 18% |
|   | Anise Oil | 33% | | | |
| 8 | Rosemary Oil | 28% | Ethanol (95%) | 100% | 61.1% |
|   | Anise Oil | 5% | | | |

TABLE 1-continued

| Example Number | Percentage (v/v) Volatile Oil | | Diluent (to 100% v/v) | Percentage Lice Killed | Percentage Eggs Killed |
|---|---|---|---|---|---|
| 9 | Rosemary Oil | 5% | Ethanol (95%) | 100% | 88.9% |
|   | Anise Oil | 28% | | | |
| 10 | Rosemary Oil | 16.5% | Ethanol (95%) | 100% | 76.3% |
|   | Anise Oil | 16.5% | | | |

It has therefore been desirable to find a pharmaceutical or veterinary composition which has the desired anti-insect properties, in which a lower concentration of volatile oils may be used and which has no adverse effect on the skin.

The present invention thus consists in a pharmaceutical or veterinary composition comprising:

a) one or more volatile oils (as herein defined);
b) one or more alcohol; and
c) one or more fixed oil (as herein defined) and/or one or more emollient ester of fatty acid derived from the vegetable oils.

The composition according to the present invention is preferably a solution.

Suitable volatile oils are, e.g., anise oil, calendula oil, quassia oil, rosemary oil and Sassafras oil.

Suitable alcohols are, e.g., ethanol and isopropyl alcohol.

Suitable fixed oils are, e.g., almond oil, avocado oil, maize oil, olive oil, peanut oil, soya oil, sunflower oil, sesame seed oil and Safflower oil.

Suitable esters (of the kind defined above) are, e.g., medium chain triglycerides (MCT), caprylic/capric triglyceride; isopropyl myristate; propylene glycol dicaprylate—dicaprate; and isopropyl palmitate. MCT are e.g. those as defined in German Pharmacopea, 8th Edition.

The amounts of each ingredient present in the composition according to the present invention may vary according to the specific ingredient utilized composition suitably comprise a) 0.5–50%, preferably 5–30% of volatile oil;
b) 10–60%, preferably 20–40% of alcohol; and
c) 10–85%, preferably 20–60% of a fixed oil and/or of the ester. (All percentages and v/v).

Some compositions according to the present invention were prepared by admixing the various ingredients. The anti-lice activity of a number of said compositions were tested in the same manner as previously described. The results are shown in Table 2.

TABLE 2

| Example Number | Percentage (v/v) Volatile Oil | | Diluent (% v/v) | | Percentage Lice Killed | Percentage Eggs Killed |
|---|---|---|---|---|---|---|
| 12 | Rosemary Oil | 15% | Olive Oil | 20% | 100% | 17.2% |
|    | Anise Oil    | 15% | *MCT       | 20% |      |       |
|    |              |     | Isopropanol| 30% |      |       |
| 13 | Rosemary Oil | 15% | Olive Oil  | 35% | 32%  | —     |
|    | Anise Oil    | 15% | MCT        | 35% |      |       |
| 14 | Rosemary Oil | 5%  | Olive Oil  | 25% | 99%  | 21%   |
|    | Anise Oil    | 15% | MCT        | 25% |      |       |
|    |              |     | Isopropanol| 30% |      |       |
| 15 | Rosemary Oil | 5%  | Olive Oil  | 40% | 15%  | —     |
|    | Anise Oil    | 15% | MCT        | 40% |      |       |
| 16 | Rosemary Oil | 5%  | Olive Oil  | 30% | 89%  | —     |
|    | Anise Oil    | 5%  | MCT        | 30% |      |       |
|    |              |     | Isopropanol| 30% |      |       |
| 17 | Rosemary Oil | 15% | Olive Oil  | 25% | 94%  | —     |
|    | Anise Oil    | 5%  | MCT        | 25% |      |       |
|    |              |     | Isopropanol| 30% |      |       |
| 18 | Rosemary Oil | 10% | Olive Oil  | 25% | 94%  | —     |
|    | Anise Oil    | 10% | MCT        | 25% |      |       |
|    |              |     | Isopropanol| 30% |      |       |
| 19 | Rosemary Oil | 5%  | Olive Oil  | 10% | 97.3%| 40.6% |
|    | Anise Oil    | 15% | Ethanol (95%) | 35% |   |       |
|    |              |     | MCT        | 30% |      |       |
|    |              |     | Isopropanol| 5%  |      |       |
| 20 | Rosemary Oil | 5%  | MCT        | 40% | 93%  | 56.8% |
|    | Anise Oil    | 15% | Isopropanol| 40% |      |       |
| 21 | Rosemary Oil | 5%  | MCT        | 40% | 90%  | 41.2% |
|    | Anise Oil    | 15% | Ethanol (95%) | 40% |   |       |
| 22 | Rosemary Oil | 5%  | MCT        | 55% | 98.7%| 58.9% |
|    |              |     | Isopropanol| 40% |      |       |
| 23 | Anise Oil    | 15% | MCT        | 45% | 100% | 59.6% |
|    |              |     | Isopropanol| 40% |      |       |

S* MCT = Medium Chain Triglycerides

The MCT utilized was Estasan$^R$ manufactured by OS Industries APS, Copenhagen. Some of these preparations were tried on human volunteers and they did not cause the burning sensation or reddening of the skin associated with high concentration of volatile oils.

What is claimed is:

1. A pharmaceutical or veterinary composition comprising:
   (a) at least one volatile oil selected from the group consisting of anise oil, calendula oil, quassia oil, rosemary oil and sassafras oil, said oil being present at a concentration in a range of from about 5% to about 50% volume per volume;
   (b) at least one alcohol being present at a concentration in a range of from about 20% to about 60% volume per volume;
   c) at least one ingredient selected from the group consisting of fixed oil and emollient ester of fatty acid derived from vegetable oils, said at least one ingredient being present at a concentration in a range of from about 10% to about 60% volume per volume.

2. The composition according to claim 1, wherein the alcohol is selected from the group consisting of ethanol and isopropyl alcohol.

3. The composition according to claim 7, wherein the fixed oil is selected form the group consisting of almond oil, avocado oil, maize oil, olive oil, peanut oil, soya oil, sunflower oil, sesame seed oil and safflower oil.

4. The composition according to claim 1, wherein the ester is selected from the group consisting of medium chain triglycerides, caprylic/capric triglycerides, isopropyl myristate, propylene glycol dicaprylate-dicaprate and isopropyl palmitate.

5. The composition according to claim 1, wherein said volatile oil is present at a concentration in a range of from about 5% to about 30% volume per volume.

6. The composition according to claim 1, wherein said alcohol is present at a concentration in a range of from about 20% to about 40% volume per volume.

7. A pharmaceurical or veterinary composition comprising:
   (a) at least one volatile oil selected from the group consisting of anise oil, calendula oil, quassia oil and sassafras oil, said volatile oil being present at a concentration in a range of from about 0.5% to about 50% volume per volume;
   (b) at least one alcohol selected from the group consisting of ethanol and isopropyl alcohol, said alcohol being present at a concentration in a range of from about 20% to about 60% volume per volume; and
   (c) at least one ingredient selected from the group consisting of fixed oil and emollient ester of fatty acid derived from vegetable oil, said at least one ingredient being present at a concentration in a range of from about 10% to about 60% volume per volume.

8. A pharmaceutical or veterinary composition comprising:
   (a) at least one volatile oil selected from the group consisting of anise oil, calendula oil, quassia oil, and sassafras oil, said oil being present at a concentration in a range of from about 0.5.% to about 50% volume per volume,
   (b) at least one alcohol selected from the group consisting of ethanol and isopropyl alcohol, said alcohol being present at a concentration in a range of from about 20% to about 60% volume per volume; and
   (c) at least one ingredient selected from the group consisting of fixed oil and emollient ester of fatty acid derived from vegetable oils, said fixed oil being selected from the group consisting of almond oil, avocado oil, maize oil, olive oil, peanut oil, soya oil, sunflower oil, scsame seed oil and safflower oil, said at least one ester being selected from the group consisting of medium chain triglycerides, caprylic/capric triglycerides, isopropyl myristate, propylene glycol dicaprylate-dicaprate and isopropyl palmitate and said at least one ingredient being present at a concentration in a range of from about 10% to about 60% volume per volume.

9. A pharmaceutical or veterinary composition comprising:
   (a) anise oil being present at a concentration in a range of from about 10% to about 20% volume per volume;
   (b) isopropyl alcohol bring present at a concentration in a range of from about 30% to about 50% volume per volume; and
   (c) at least one ingredient selected from the group consisting of fixed oil and emollient ester of fatty acid derived from vegetable oils, said at least one ingredient being present at a concentration in a range of from about 35% to about 45% volume per volume.

10. The composition according to claim 7, wherein the volatilc oil is selected from the group consisting of anise oil, calendula oil, quassia oil, rosemary oil and sassafras oil.

* * * * *